United States Patent
Moctezuma de la Barrera et al.

(10) Patent No.: US 12,220,281 B2
(45) Date of Patent: Feb. 11, 2025

(54) ULTRASOUND BONE REGISTRATION WITH LEARNING-BASED SEGMENTATION AND SOUND SPEED CALIBRATION

(71) Applicant: MAKO Surgical Corp., Weston, FL (US)

(72) Inventors: José Luis Moctezuma de la Barrera, Freiburg (DE); Mehrdad Salehi, Munich (DE); Raphael Prevost, Munich (DE); Wolfgang Wein, Munich (DE)

(73) Assignee: MAKO Surgical Corp., Weston, FL (US)

( * ) Notice: Subject to any disclaimer, the term of this patent is extended or adjusted under 35 U.S.C. 154(b) by 64 days.

(21) Appl. No.: 18/205,734

(22) Filed: Jun. 5, 2023

(65) Prior Publication Data
US 2023/0301633 A1  Sep. 28, 2023

Related U.S. Application Data

(63) Continuation of application No. 15/999,152, filed on Aug. 16, 2018, now Pat. No. 11,701,090.
(Continued)

(51) Int. Cl.
*A61B 8/08* (2006.01)
*A61B 6/00* (2024.01)
(Continued)

(52) U.S. Cl.
CPC .......... *A61B 8/5207* (2013.01); *A61B 6/5247* (2013.01); *A61B 8/0875* (2013.01);
(Continued)

(58) Field of Classification Search
None
See application file for complete search history.

(56) References Cited

U.S. PATENT DOCUMENTS 6,352,512 B1 *  3/2002  Wilson ................... A61B 8/587
                                                              600/449
6,775,404 B1    8/2004  Pagoulatos et al.
(Continued)

FOREIGN PATENT DOCUMENTS

KR     20150118732 A  * 10/2015
WO      2017038300 A1    3/2017

OTHER PUBLICATIONS

Wein, W., & Khamene, A. (Mar. 2008). Image-based method for in-vivo freehand ultrasound calibration. In Medical Imaging 2008: Ultrasonic Imaging and Signal Processing (vol. 6920, pp. 179-185). SPIE. (Year: 2008).*

(Continued)

*Primary Examiner* — Jason M Ip
*Assistant Examiner* — Renee C Langhals
(74) *Attorney, Agent, or Firm* — Howard & Howard Attorneys PLLC

(57) ABSTRACT

Systems and methods for calibrating ultrasound imaging directed towards a bone region. An ultrasound imaging device generates a first steered frame and a second steered frame, wherein the first steered frame and the second steered frame are directed towards the bone region at different angles from one another and are superimposed with one another. Parameters of each of the first steered frame and the second steered frame are applied to a cost function that outputs an estimated propagation speed of ultrasound waves to the bone region for optimizing an appearance of the first steered frame and the second steered frame. The ultrasound imaging device is calibrated based on the estimated propagation speed.

14 Claims, 4 Drawing Sheets

Related U.S. Application Data

(60) Provisional application No. 62/546,158, filed on Aug. 16, 2017.

(51) Int. Cl.
  A61B 6/03 (2006.01)
  A61B 8/00 (2006.01)
  A61B 34/10 (2016.01)
  G06T 7/11 (2017.01)
  G06T 7/33 (2017.01)

(52) U.S. Cl.
  CPC .......... *A61B 8/4416* (2013.01); *A61B 8/5223* (2013.01); *A61B 8/5238* (2013.01); *A61B 34/10* (2016.02); *G06T 7/33* (2017.01); *A61B 6/032* (2013.01); *A61B 8/58* (2013.01); *A61B 2034/105* (2016.02); *G06T 7/11* (2017.01); *G06T 2207/10132* (2013.01)

(56) References Cited

U.S. PATENT DOCUMENTS

| | | |
|---|---|---|
| 7,725,162 B2 | 5/2010 | Malackowski et al. |
| 7,840,256 B2 | 11/2010 | Lakin et al. |
| 8,622,915 B2 | 1/2014 | Dala-Krishna |
| 9,381,085 B2 | 7/2016 | Axelson, Jr. et al. |
| 9,480,534 B2 | 11/2016 | Bowling et al. |
| 9,707,043 B2 | 7/2017 | Bozung |
| 9,921,712 B2 | 3/2018 | Lightcap et al. |
| 2006/0142657 A1 | 6/2006 | Quaid et al. |
| 2009/0089034 A1 | 4/2009 | Penney et al. |
| 2012/0330429 A1 | 12/2012 | Axelson, Jr. et al. |
| 2013/0060278 A1 | 3/2013 | Bozung et al. |
| 2013/0144135 A1 | 6/2013 | Mahfouz et al. |
| 2013/0211230 A1 | 8/2013 | Sperling |
| 2014/0039517 A1 | 2/2014 | Bowling et al. |
| 2014/0073907 A1 | 3/2014 | Kumar et al. |
| 2015/0173723 A1 | 6/2015 | Bates et al. |
| 2016/0030000 A1* | 2/2016 | Sandhu ................ A61B 8/5207 600/448 |
| 2017/0000577 A1 | 1/2017 | Bowling et al. |
| 2017/0112476 A1 | 4/2017 | Belevich et al. |
| 2017/0217102 A1 | 8/2017 | Mansi et al. |
| 2017/0245947 A1 | 8/2017 | Bozung et al. |
| 2018/0303463 A1 | 10/2018 | Zanin et al. |
| 2018/0333207 A1 | 11/2018 | Moctezuma De La Barrera |
| 2018/0374209 A1* | 12/2018 | Patil ........................ G06N 3/084 |
| 2019/0069882 A1 | 3/2019 | Moctezuma de la Barrera et al. |

OTHER PUBLICATIONS

KR20150118732A translation—translated on Sep. 25, 2024 (Year: 2015).*
Abstract of Jones, D.R. et al., "Direct Global Optimization Algorithm", Encyclopedia of Optimization, Chapter 93, 2001, 5 pages.
Baka, N. et al., "Machine Learning Based Bone Segmentation in Ultrasound", MICCAI Workshop, 2016, pp. 16-25.
Cernazanu-Glavan, C. et al., "Segmentation of Bone Structure in X-Ray Images Using Convolutional Neural Network", Adv. Electr. Comput. Eng., vol. 13, No. 1, 2013, pp. 87-94.
Elfring, R. et al., "Assessment of Optical Localizer Accuracy for Computer Aided Surgery Systems", Comput. Aided Surg., vol. 15, Nos. 1-3, 2010, pp. 1-12.
English language abstract and machine-assisted English translation for WO 2017/038300 extracted from espacenet.com database on Dec. 19, 2018, 28 pages.
Hacihaliloglu, I. et al., "Automatic Adaptive Parameterization in Local Phase Feature-Based Bone Segmentation in Ultrasound", Ultrasound Med. Biol., vol. 37, No. 10, 2011, pp. 1689-1703.
He, K. et al., "Guided Image Filtering" IEEE Trans. Pattern Anal. Mach. Intell., vol. 35, No. 6, 2013, pp. 1397-1409.
Huang, X. et al., "Dynamic 2D Ultrasound and 3D CT Image Registration of the Beating Heart", IEEE Transactions on Medical Imaging, vol. 28, No. 8, 2009, pp. 1179-1189.
International Search Report for Application No. PCT/IB2018/056189 dated Dec. 10, 2018, 4 pages.
Jaeger, M. et al., "Computed Ultrasound Tomography in Echo Mode (CUTE) of Speed of Sound for Diagnosis and for Aberration Correction in Pulse-Echo Sonography", Proceedings of SPIE, vol. 9040, 2014, 12 pages.
Jain, A.K. et al., "Understanding Bone Responses in B-Mode Ultrasound Images and Automatic Bone Surface Extraction Using a Bayesian Probabilistic Framework", Proceedings of SPIE Medical Imaging, 2004, pp. 131-142.
Jones, D.R. et al., "Lipschitzian Optimization Without the Lipschitz Constant", Journal of Optimization Theory and Applications, vol. 79, No. 1, 1993, pp. 157-181.
Long, J. et al., "Fully Convolutional Networks for Semantic Segmentation", Proceedings of IEEE Conference: CVPR, 2015, pp. 3431-3440.
Miccai, "Video and Presentations from 20th International Conference on Medical Image Computing and Computer Assisted Intervention", Sep. 10-14, 2017, Quebec, Canada, 3 pages, web link to presentations: http://www.miccai2017.org/.
Nelder, J.A. et al., "A Simplex Method for Function Minimization", The Computer Journal, vol. 7, No. 4, 1965, pp. 308-313.
Ozdemir, F. et al., "Grahical Modeling of Ultrasound Propagation in Tissue for Automatic Bone Segmentation", MICCAI, vol. 9901, 2016, pp. 256-264.
Ronneberger, O. et al., "Convolutional Networks for Biomedical Image Segmentation", MICCAI, LNCS, vol. 9351, 2015, pp. 234-241.
Salehi, Mehrdad et al., "Precise Ultrasound Bone Registration with Learning-Based Segmentation and Speed of Sound Calibration", Sep. 4, 2017, 8 pages.
Shin, H.C. et al., "Estimation of Speed of Sound in Dual-Layered Media Using Medical Ultrasound Image Deconvolution", Ultrasonics, vol. 50, No. 7, 2010, pp. 716-725.
Wein, W. et al., "Automatic Bone Detection and Soft Tissue Aware Ultrasound-CT Registration for Computer-Aided Orthopedic Surgery", IJCARS, vol. 10, No. 6, 2015, pp. 971-979.
Wein, W. et al., "Image-Based Method for In-Vivo Freehand Ultrasound Calibration", Proceedings of SPIE, Medical Imaging, vol. 6920, 2008, pp. 69200K-1 through 69200K-7.
Wein, Wolfgang et al., "Automatic Bone Detection and Soft Tissue Aware Ultrasound-CT Registration for Computer-Aided Orthopedic Surgery", International Journal of Computer-Assisted Radiology and Surgery, vol. 10, No. 6, Jun. 1, 2015, pp. 971-979.

* cited by examiner

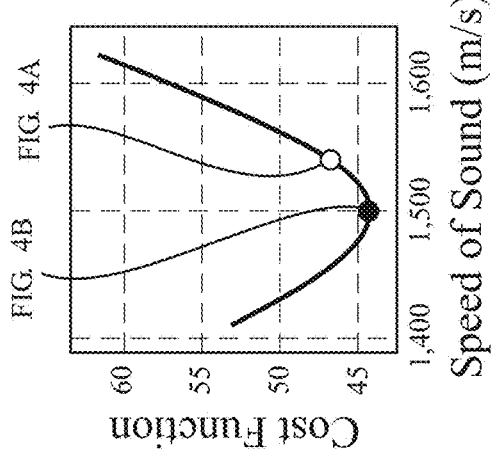
FIG. 4A
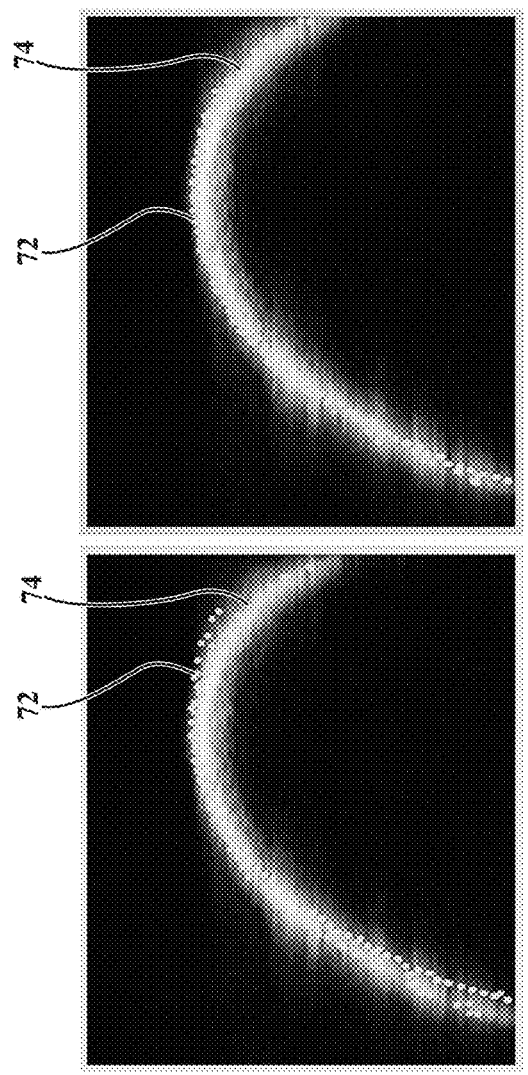
FIG. 4B
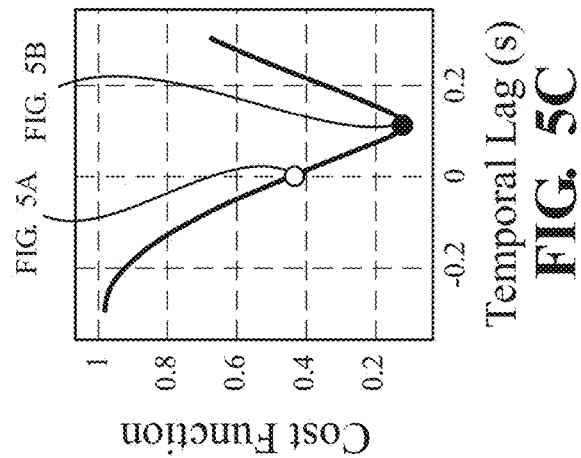
FIG. 4C
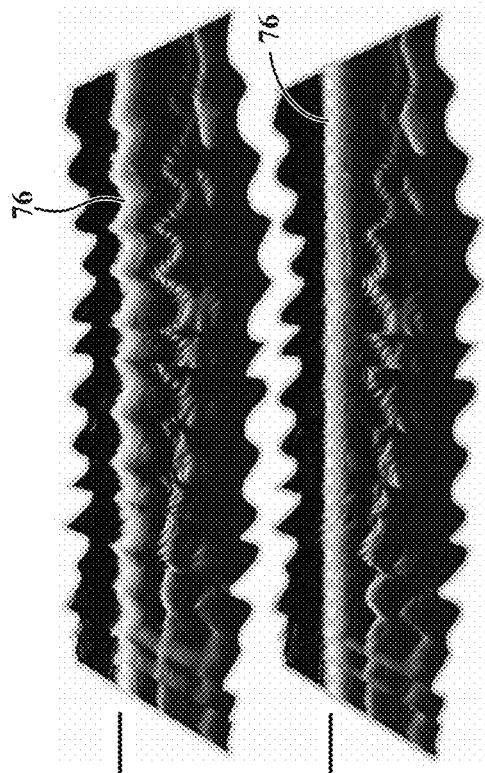
FIG. 5A
FIG. 5B
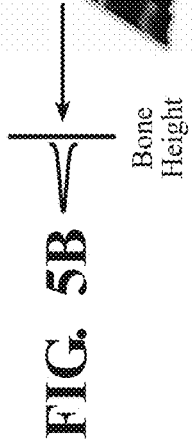
FIG. 5C

ULTRASOUND BONE REGISTRATION WITH LEARNING-BASED SEGMENTATION AND SOUND SPEED CALIBRATION

CROSS REFERENCE TO RELATED APPLICATIONS

The subject application is a continuation of U.S. patent application Ser. No. 15/999,152, filed Aug. 16, 2018, which claims priority to and the benefit of U.S. Provisional Patent App. No. 62/546,158, filed on Aug. 16, 2017, the contents of which is hereby incorporated by reference in its entirety.

BACKGROUND

Navigated surgery in the orthopedic domain often requires registration of a reconstructed image of a bone surface to a co-modality image, such as computed tomography (CT) or magnetic resonance imaging (MRI) scan. Conventional techniques established in the clinical routine usually reconstruct the image solely on an area of the bone surface contacted with a tracked pointer following exposure at the surgical site. As an alternative, ultrasound is becoming increasingly used in navigated surgery and registration-based applications to image and reconstruct a larger area of the bone surface. However, spatial and temporal information quality of ultrasound is relatively inferior to other modalities primary due to speed-of-sound variations and refractions, and tissue deformation. Further challenges are associated with many conventional tracked ultrasound systems, as they often require a custom image processing algorithm to detect the bone surface in individual ultrasound frames. These systems and methods have severe limitations with either insufficient detection coverage of the visible bone surface, or the occurrence of false positive detections.

Therefore, a need exists in the art for a navigated surgery system using ultrasound with an improved workflow to register ultrasound imaging to a co-modality imaging that overcomes one or more of the aforementioned disadvantages.

SUMMARY

This Summary introduces a selection of concepts in a simplified form that are further described below in the Detailed Description below. This Summary is not intended to limit the scope of the claimed subject matter nor identify key features or essential features of the claimed subject matter.

One example of an ultrasound imaging system is provided, which comprises: an ultrasound imaging device comprising a transducer configured to generate ultrasound imaging of a bone region by propagation of ultrasound waves to the bone region; and one or more controllers coupled to the ultrasound imaging device and being configured to: generate, with the ultrasound imaging device, a first steered frame and a second steered frame, wherein the first steered frame and the second steered frame are directed towards the bone region at different angles from one another and are superimposed with one another; apply parameters of each of the first steered frame and the second steered frame to a cost function configured to output an estimated propagation speed of ultrasound waves to the bone region that optimizes an appearance of the first steered frame and the second steered frame; and calibrate the ultrasound imaging device based on the estimated propagation speed.

One example of a method is provided of operating an ultrasound imaging system, the ultrasound imaging system comprising an ultrasound imaging device including a transducer configured to generate ultrasound imaging of a bone region by propagation of ultrasound waves to the bone region, and one or more controllers coupled to the ultrasound imaging device, the method comprising the one or more controllers: generating, with the ultrasound imaging device, a first steered frame and a second steered frame, wherein the first steered frame and the second steered frame are directed towards the bone region at different angles from one another and are superimposed with one another; applying parameters of each of the first steered frame and the second steered frame to a cost function that outputs an estimated propagation speed of ultrasound waves to the bone region for optimizing an appearance of the first steered frame and the second steered frame; and calibrating the ultrasound imaging device based on the estimated propagation speed.

One example of a computer-implemented method is provided for calibrating ultrasound imaging directed towards a bone region, the method comprising: generating, with the ultrasound imaging, a first steered frame and a second steered frame, wherein the first steered frame and the second steered frame are directed towards the bone region at different angles from one another and are superimposed with one another; applying parameters of each of the first steered frame and the second steered frame to a cost function that outputs an estimated propagation speed of ultrasound waves to the bone region for optimizing an appearance of the first steered frame and the second steered frame; and calibrating the ultrasound imaging based on the estimated propagation speed.

One example of a method for automatically registering ultrasound imaging of an object with co-modality imaging of the object is provided. The method includes segmenting the ultrasound imaging with a convolutional neural network to detect a surface of the object. The ultrasound image is calibrated to reflect a variation in propagation speed of the ultrasound waves through the object by comparing first and second steered frames of the ultrasound imaging with a third frame of the ultrasound imaging that is angled between the first and second steered frames. The ultrasound image is temporally calibrated with respect to a tracking coordinate system by creating a point cloud of the surface and calculating a set of projection values of the point cloud to a vector. The segmented and calibrated ultrasound imaging is automatically registered to the co-modality imaging.

One example of a system for automatically registering ultrasound imaging of an object with co-modality imaging of the object is provided. The system includes an imaging device and one or more controllers. The imaging device is configured to generate the ultrasound imaging. The controller(s) are configured to segment the ultrasound imaging with the convolutional neural network to detect the surface of the object, calibrate the ultrasound imaging to reflect the variation in propagation speed of the ultrasound waves through the object by comparing the first and second steered frames of the ultrasound imaging with the third frame of the ultrasound imaging that is angled between to the first and second steered frames, and temporally calibrate the ultrasound imaging with respect to the tracking coordinate system by creating the point cloud of the surface and calculating the set of projection values of the point cloud to the vector, and automatically register the ultrasound imaging to the co-modality imaging.

One example of a method for segmenting ultrasound imaging generated by propagating ultrasound waves along a plurality of scanlines through the object is provided. The method includes generating a probability map of the ultrasound imaging with the convolutional neural network. A surface of the object is extracted from the probability map for each of the scanlines.

One example of a method for calibrating ultrasound imaging is provided. The method includes identifying a first steered frame of the ultrasound imaging, identifying a second steered frame of the ultrasound imaging, and identifying a third frame of the ultrasound imaging that is angled between the first and second steered frames. The method includes computing a first difference between the first steered frame and the third frame, and a second difference between the second steered frame and the third frame. A sum of the first and second differences is computed. The sum is optimized to minimize a cost function. A propagation speed of the ultrasound waves through the object is estimated based on the optimized sum. The ultrasound imaging is calibrated based on the estimated propagation speed.

One example of a method for temporally calibrating ultrasound imaging of an object with respect a tracking coordinate system. The ultrasound imaging is generated by propagating ultrasound waves along a plurality of scanlines through the object, and a surface of the object is extracted by segmentation. The method includes extracting a point cloud of the object surface. A set of projection values is calculated by projecting the point cloud to a 3D vector that is oriented relative to the scanlines. A temporal lag is computed for the ultrasound imaging based on the set of projection values.

The techniques described herein advantageously provide a workflow to accurately register ultrasound imaging to a co-modality imaging based on an automatic and real-time image segmentation and calibration. A convolutional neural network (CNN) provides fast, robust, and accurate bone segmentation of the ultrasound imaging in real-time. The real-time detection allows for: (i) automatic speed-of-sound analysis; (ii) compensation methods based on steered compound ultrasound imaging around the detected bone; (iii) automatic temporal calibration between a tracking coordinate system and the ultrasound imaging; and (iv) automatic adaptation of focus, depth and frequency of the ultrasound imaging. Techniques based on deep learning overcome the aforementioned challenges and produce accurate bone probability maps in a more robust way that standard feature-based methods. Examples provided advantageously result in overall errors of less than one millimeter.

The system and methods may exhibit advantages and provide technical solutions other than those described herein.

BRIEF DESCRIPTION OF THE DRAWINGS

Other aspects, features, and advantages of the present invention will become more fully apparent from the detailed description, the appended claims, and the accompanying drawings wherein like reference numerals identify similar or identical elements.

FIG. 4A shows a schematic visualization of two point clouds extracted from two ultrasound sweeps acquired at different angles before calibration for the speed of sound.

FIG. 4B shows a schematic visualization of two point clouds extracted from two ultrasound sweeps acquired at different angles after calibration for the speed of sound.

FIG. 4C plots a cost function relative to speed of sound and shows a global minimum at the optimization of the speed of sound calibration.

FIG. 5A shows a schematic reconstruction of a sample ultrasound sweep before optimization for temporal lag.

FIG. 5B shows a schematic reconstruction of a sample ultrasound sweep after optimization for temporal lag.

FIG. 5C plots a cost function relative to temporal lag and shows a global minimum at the optimization for the temporal lag calibration.

DETAILED DESCRIPTION

Figure 1:
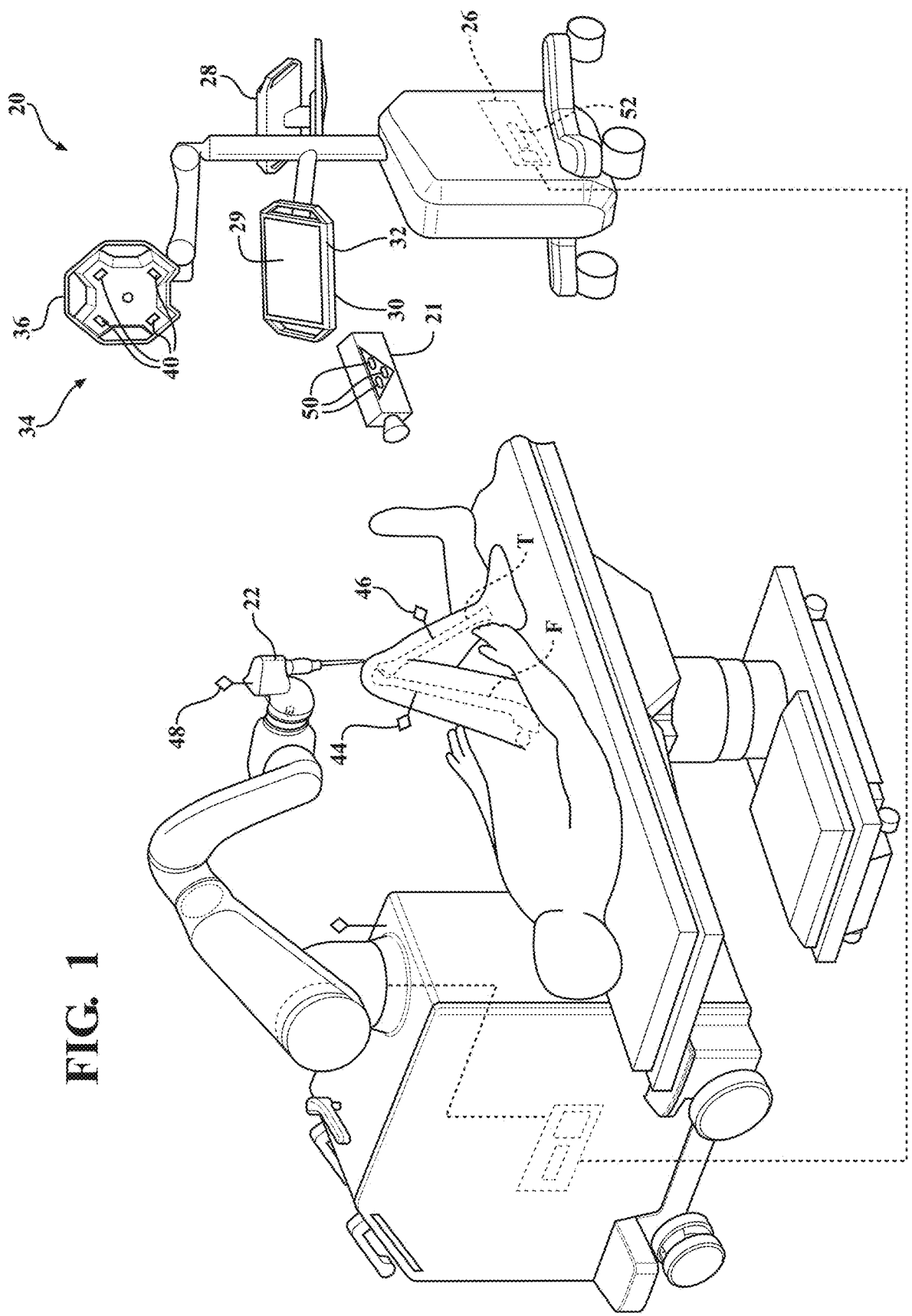
FIG. 1 is a perspective view of a navigation system being used in conjunction with a robotic manipulator with the navigation system using a workflow for registering ultrasound imaging to co-modality imaging in accordance with an embodiment of the present disclosure.

FIG. 1 shows an embodiment of a surgical navigation system 20 for use with embodiments of the workflow to be described. The surgical navigation system 20 is shown in a surgical setting, such as an operating room of a medical facility, and arranged to track movement of various objects in the operating room. Such objects include, for example, an ultrasound device 21, a surgical instrument 22, and trackers 44, 46 coupled to, for example, a femur F and a tibia T of a patient. In the illustrated example, the ultrasound device 21 is a handheld probe movable in proximity to the anatomy of interest. Alternatively, the ultrasound device 21 may be attached to a robotic arm. One or more trackers 50 may be coupled to the ultrasound device 21. A tracker 48 may also be coupled to the surgical instrument 22. The trackers 44, 46 may be attached to the femur F in the manner shown in U.S. Pat. No. 7,725,162, entitled Surgery System, hereby incorporated by reference in its entirety. Optical sensors 40 of the localizer 34, for example, three separate high resolution charge-coupled devices (CCD) to detect infrared (IR) signals, track the trackers 44, 46, 48, 50. A camera unit 36 includes a camera controller 42 in communication with the optical sensors 40 to receive signals from the optical sensors 40. The camera unit 36 receives optical signals from the ultrasound device 21 and the trackers 44, 46, 48, 50. The camera unit 36 outputs to the processor 52 signals relating to the position of the ultrasound device 21 and the trackers 44, 46, 48, 50 relative to the localizer 34. Position and orientation signals and/or data are transmitted to the navigation computer 26 for purposes of tracking the objects. A navigation computer 26 includes a navigation interface having one or more displays 28, 29 and input devices 30, 32 for inputting information into the navigation computer 26 or otherwise select or control certain aspects of the navigation computer 26. The navigation computer 26 also includes the processor 52 such as one or more microprocessors or multi-processor systems to control operation of the navigation computer 26. The navigation system 20 communicates position and/or orientation data to the robotic control system. The position and/or orientation data is indicative of a position and/or orientation of the surgical instrument 22 relative to the anatomy. This communication provides closed loop control to control cutting of the anatomy such that the cutting occurs within a predefined path or anatomical boundary.

In the embodiment shown in FIG. 1, the surgical instrument 22 is an end effector of a surgical manipulator similar to that described in U.S. Pat. No. 9,480,534, entitled "Navigation System for use with a Surgical Manipulator Operable in Manual or Semi-Autonomous Modes," and U.S. Pat. No. 9,480,534 entitled, "Navigation System for Removing a Volume of Tissue from a Patient", the disclosures of each is hereby incorporated by reference in its entirety. The robotic surgical system may include the manipulator including a plurality of arms and the surgical instrument 22 carried by at least one of the plurality of arms. A robotic control system controls or constrains movement of the cutting tool in at least five degrees of freedom.

In other embodiments, the surgical instrument 22 may be manually positioned by only the hand of the user, without the aid of any cutting guide, jib, or other constraining mechanism such as a manipulator or robot. One such suitable surgical instrument, for example, is described in U.S. Pat. No. 9,707,043, entitled, "Surgical Instrument Including Housing, a Cutting Accessory that Extends from the Housing and Actuators that Establish the Position of the Cutting Accessory Relative to the Housing," hereby incorporated by reference in its entirety. In other systems, the instrument 22 has a cutting tool that is movable in three degrees of freedom relative to a handheld housing and is manually positioned by the hand of the surgeon, without the aid of cutting jig, guide arm or other constraining mechanism. Such systems are shown in U.S. Pat. No. 9,707,043, entitled, "Surgical Instrument Including Housing, a Cutting Accessory that Extends from the Housing and Actuators that Establish the Position of the Cutting Accessory Relative to the Housing," hereby incorporated by reference in its entirety. The system includes a hand held surgical cutting instrument having a cutting tool. A control system controls movement of the cutting tool in at least three degrees of freedom using internal actuators/motors. In such an embodiment, the navigation system 20 communicates with the control system of the hand held surgical cutting instrument. The navigation system 20 communicates position and/or orientation data to the control system. The position and/or orientation data is indicative of a position and/or orientation of the instrument 22 relative to the anatomy. The position and/or orientation data is more accurately determined with the workflow 100 as described throughout the present disclosure. This communication provides closed loop control to control cutting of the anatomy such that the cutting occurs within a predefined boundary (the term predefined boundary includes predefined trajectory, volume, line, other shapes or geometric forms, and the like).

The workflow and techniques can be utilized with various other techniques relating to ad-hoc intraoperative surgical planning, such as those techniques described in U.S. patent application Ser. No. 15/952,810, entitled "Computer Aided Planning of Orthopaedic Surgeries," the contents of which is incorporated by reference in its entirety.

When tracking both the instrument 22 and the anatomy being cut in real time in these systems, the need to rigidly fix anatomy in position can be eliminated. Since both the surgical instrument 22 and anatomy are tracked, control of the surgical instrument 22 can be adjusted based on relative position and/or orientation of the surgical instrument 22 to the anatomy. Also, representations of the surgical instrument 22 and anatomy on the display(s) 28, 29 can move relative to one another—to emulate their real world motion. In one embodiment, each of the femur F and tibia T has a target volume of material that is to be removed by the working end of the surgical instrument 22. The target volumes are defined by one or more boundaries. The boundaries define the surfaces of the bone that should remain after the procedure. In some embodiments, the system 20 tracks and controls the surgical instrument 22 to ensure that working end, e.g., bur, only removes the target volume of material and does not extend beyond the boundary, as disclosed in U.S. Pat. No. 9,921,712 entitled, "System and Method for Providing Substantially Stable Control of a Surgical Tool", hereby incorporated by reference in its entirety. Control of the surgical instrument 22 may be accomplished by utilizing, at least in part, the registered intraoperative ultrasound image to the pre-operative imaging with the workflow 100 to be described. With the improved registration, the surgical instrument 22 or the manipulator to which it is mounted, may be controlled so that only desired material is removed.

Any aspects of the workflow 100 described herein can be executed on any of the computers, or controllers described herein. The computers or controllers can comprise a non-transitory computer-readable medium, having instructions stored therein. When the instructions are executed by one or more processor, the instructions implement any aspect of the workflow.

Co-modality imaging of the femur F and tibia T (or of other tissues in other embodiments) is acquired. The co-modality imaging may be based on CT scans, MRI scans, radiological scans, or other suitable imaging of the patient's anatomy of interest. The co-modality imaging may be acquired preoperatively or intraoperatively.

The ultrasound imaging may include propagating ultrasonic waves along a plurality of scanlines through the object or anatomy of interest. The incident waves are reflected from objects or anatomy of differing characteristics with the reflected waves detectable by the ultrasound device 21. The reflected waves may be processed by the navigation system 20 to generate frames that are combined to display in real time the ultrasound imaging. In one example, the ultrasound device 21 is the aforementioned hand held probe is moved relative the anatomy of interest to perform a "sweep." The ultrasound imaging is obtained intraoperatively.

Figure 6:
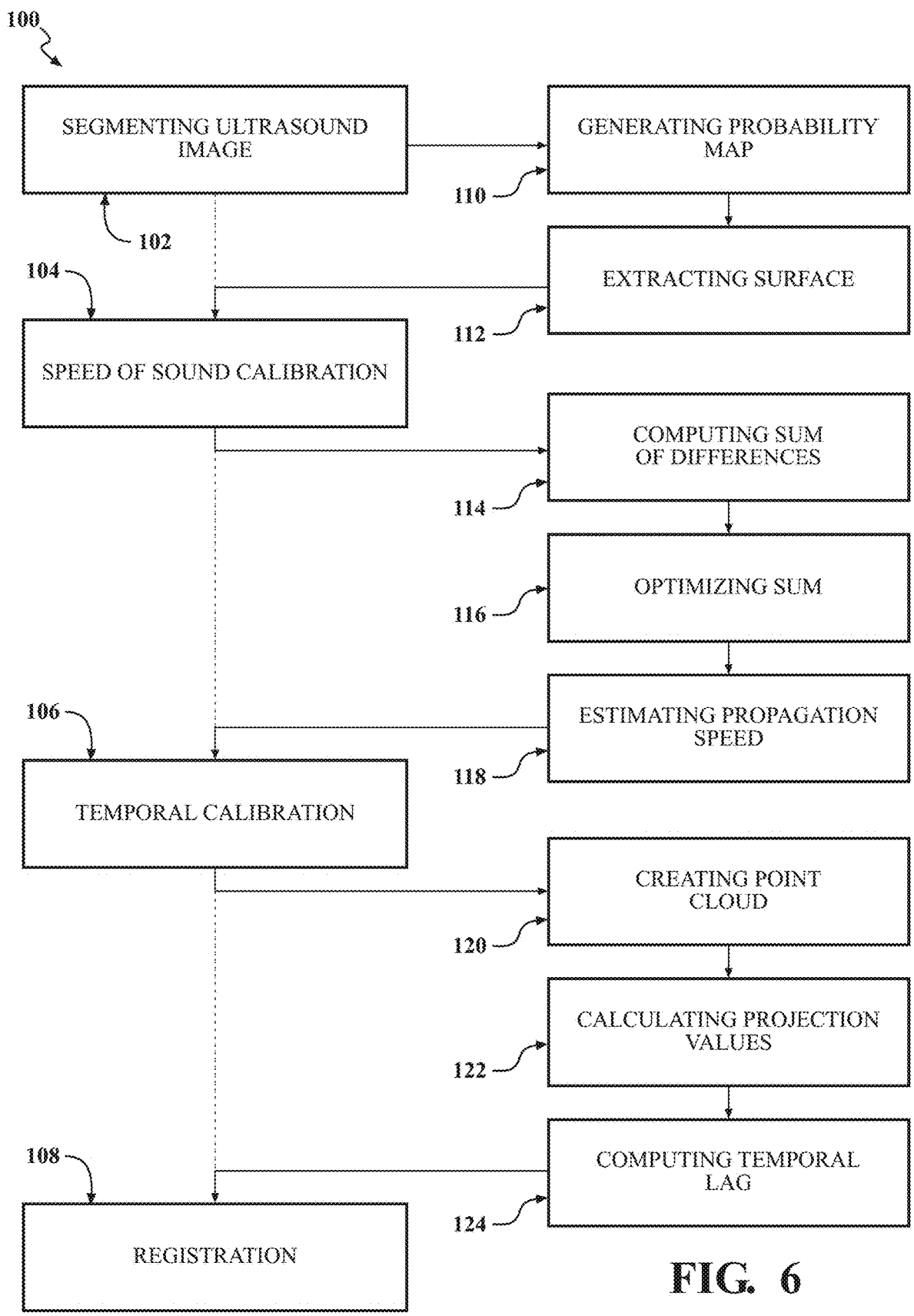
FIG. 6 is a flowchart of a workflow for workflow for registering ultrasound imaging to co-modality imaging

FIG. 6 is a flowchart of a sample workflow 100 to be described to provide for automatic, accurate, and/or real-time segmentation and calibration of the ultrasonic imaging for registration to the co-modality imaging. The workflow 100 includes the steps of segmenting the ultrasound imaging (step 102), calibrating for variations in the speed of sound (step 104), calibrating for temporal lag (step 106), and registering the ultrasound imaging to co-modality imaging (step 108). Steps 102-106 can be performed in a sequence other than the sequence shown in FIG. 6. Moreover, steps 102-106 provide independent technical solutions and can be performed independently or with workflows other than the workflow shown in FIG. 6.

At step 102, the object surface captured in the ultrasound imaging is detected and segmented. The workflow 100 includes a surface detection algorithm using the convolutional neural network (CNN), and in certain embodiments a fully convolutional neural network (f-CNN). In other words, the ultrasound imaging is segmented with the CNN to detect a surface of the object, for example, a surface of a bone. The f-CNN is initially trained on a set of labeled images having the bone area roughly drawn by several users. In one example, the f-CNN is trained by defining multi-resolution layer combinations, such as semantic information from a deep, coarse layer with appearance information from a shallow, fine layer. The resulting f-CNN is suitably trained to engage in bone surface recognition and segmentation.

During the operative procedure, the ultrasound imaging may be processed and provided as an input image to the navigation processor 52. For example, with reference to FIG. 1, the ultrasound device 21 may be moved to a position adjacent to and in contact with the patient such that the ultrasound device 21 detects the femur F or the tibia T of the patient. A sweep of the femur F or the tibia T may be performed.

Figures 2A, 2B, 2C:
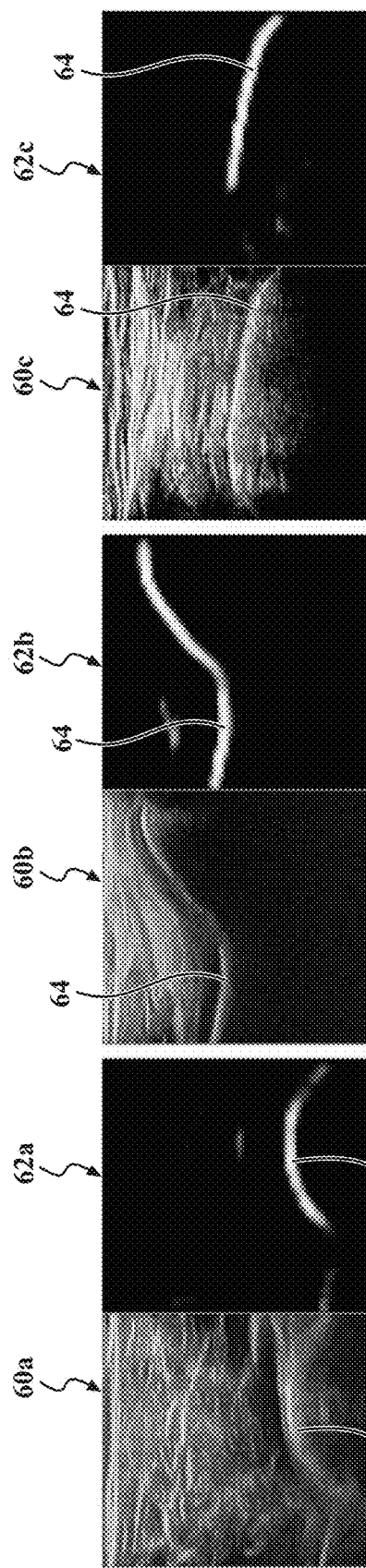
FIGS. 2A-2C show probability maps predicted a convolutional neural network executing aspects of the workflow.

The workflow includes the f-CNN analyzing the input image. In one example, the f-CNN includes a series of 3×3 convolutional layers with ReLU non-linearities and max-pooling layers, followed by deconvolutional layers and similar non-linearities. The f-CNN generates a probability map (step 110). Each of FIGS. 2A-2C shows an ultrasonic image 60a-c juxtaposed against the probability map 62a-c of the object 64 predicted by the f-CNN. The probability map 62a-c of the bone, at this point, may be considered generally "fuzzy." In illustrated embodiment shows the probability map 62a-c being the same size as the input image.

The workflow 100 includes the step of extracting the bone surface from the probability map 62a-c (step 112). In certain embodiments, the bone surface may be extracted for each scanline from the imaging. For example, the probability map 62a-c of the bone may include a maximum gradient and a maximum intensity along the scanline. The bone surface may be the center pixel between the maximum gradient and the maximum intensity along the scanline. Based on the reliability of the f-CNN, which was previously trained for deep, feed-forward processing, using only the maximum gradient and the maximum intensity is sufficient to identify the bone surface. Consequently, most outliers that may negative affect the analysis are discarded. Further, the simplicity associated with the f-CNN and using thresholding (i.e., the maximum gradient) and largest component (i.e., the maximum intensity) analysis, the workflow 100 is able to be performed in real-time, for example, at thirty images per second. In other words, the bone surface captured with ultrasound image may be detected (i.e., identified and segmented) in real-time with improvement in the speed with which the workflow 100 is performed. Furthermore, dedicated online algorithms may be leveraged during the workflow 100.

Figure 3:
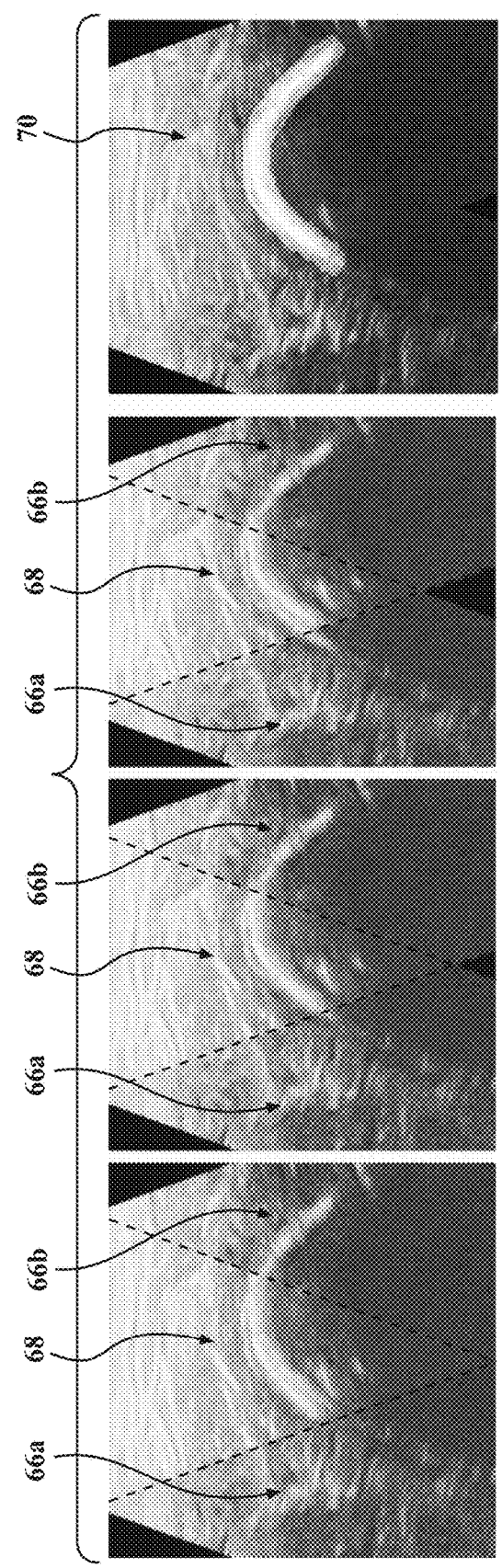
FIG. 3 illustrates steered frames of an ultrasound sweep compounded with different speeds of sound. Frames with ±10° are shown, and an effective area of similarity computation is shown and non-bone areas are masked out.

In certain instances, for example delay-sum beamforming, misalignment when imaging an object from different angles (e.g., during a sweep) results from the speed of sound expanding or compressing the images along the direction of beams. The problem may be particularly pronounced for an overlapping area of steered frames (i.e., an ultrasound frame directed at the object from different angles that results in the overlapping area). FIG. 3 demonstrates effect of speed of sound on overlapping area 68 of steered frames 66a-b, namely with the speed of sound being underestimated by ten percent, correct, and overestimated by ten percent. The workflow 100 of the present disclosure advantageously provides for speed-of-sound analysis and speed-of-sound calibration (step 102) to reflect variation in propagation speed of the ultrasound waves through the object. More particularly, the workflow 100 compensates for any expansion or compression the images along the direction of beams, thereby producing more accurate imaging prior to registration with the co-modality imaging. The speed-of-sound calibration may be provided in real-time.

The workflow 100 includes summing the differences between a first steered frame 66a and a second steered frame 66b of the ultrasound imaging (step 114), and estimating the propagation speed (step 116). The propagation speed may be estimated by optimizing the appearance of first and second steered frames 66a-b. Given the first and second steered frames I and J, respectively, the propagation speed c may include minimizing following cost function (step 116) to optimize the sum of the differences between the first and second steered frames:

$$f(I, J, c) = \frac{\sum_{p \in S} |I_p^c - J_p^c|}{|S|},$$

where S is the set of all pixels within the bone region of interest in image $I^{c-}$; $I_p^c$ and $J_p^c$ are corresponding pixel intensities in the images after compounding them with the speed of sound c. It is noted that more advanced measures of similarity do not significant alter the results.

The workflow 100 addresses challenges with comparing frames of ultrasound imaging due to reflection from most tissue boundaries and objects depending on the insonification angle. The workflow 100 provides consistency to the calibrated or optimized value of the propagation speed. Referring to FIG. 3, non-bone areas 70 are masked out (right), then each of the first and second steered frames 66a-b ($I_l$ and $I_r$) are compared to a third frame of the ultrasound imaging that is angled between the first and second steered frames. In one example, the third frame is a perpendicular image ($I_m$). More specifically, a first difference between the first steered frame and the third frame is computed, and a second difference between the second steered frame and the third frame is computed. The calibrated or optimized value for the propagation speed is calculated as $$\arg\min f(I_l,I_m,c)+f(I_r,I_m,c).$$

FIGS. 4A and 4B each shows of two point clouds 72, 74 each extracted from ultrasound sweeps acquired at a different angle with the point clouds 72, 74 superimposed on the ultrasound imaging. FIG. 4A illustrates that prior to calibration, the point clouds 72, 74 are less in alignment with the object of the ultrasound imaging based on, for example, the speed of sound expanding or compressing and its effect of speed of sound on overlapping area 68 of steered frames 66a-b. FIG. 4B illustrates that following calibration, improved shape consistency is shown between the point clouds 72, 74 and the object. FIG. 4C plots the cost function relative to the speed of sound for estimations prior to and after calibration, i.e., FIGS. 4A and 4B, respectively. FIG. 4C shows that the cost function is at a global minimum following calibration for speed of sound using the aforementioned workflow 100. Estimating the speed of sound with two frames facilitates real-time calibration with leveraging online algorithms, and further allows the workflow to be processed in real-time. Conventional methods directly comparing the two steered frames increases dissimilarities in the point-spread-function, and conventional methods requiring additional steered frames requires computing and other resources less suitable for real-time processing and leveraging of online algorithms.

As mentioned, the position of the ultrasound device 21 can be tracked by the surgical navigation system 20, for example, by the optical sensors 40 of the localizer 34 sensing the trackers 50 coupled to the ultrasound device 21. Certain inaccuracies may be associated with such systems tracking a moving probe that is concurrently obtaining intraoperative ultrasound imaging. Thus, the workflow 100 may include spatial and temporal calibration of the ultrasound imaging (step 106), and in particular to determine the relative transformation between the ultrasound device 21 and image coordinates as detected by the ultrasound device 21 (e.g., the coordinates of the segmented bone surface as adjusted for variances in the speed of sound). The automatic spatial calibration—i.e., adaptation of focus, depth and frequency of the intraoperative ultrasound imaging may include non-linear optimization that maximizes the two-dimensional ultrasound imaging from one sweep to reconstructions computed from the other sweep. Extensions to the image-based spatial calibration may be included to optimize over multiple recordings and handle more arbitrary sweep geometries.

Referring now to FIGS. 5A-5C, the temporal calibration (e.g., a temporal synchronization shift parameter) may be optimized separately. Embodiments of the workflow 100 include recording an ultrasound sweep from the bone surface while the ultrasound device 21 is slowly pushed towards the object and released several times. FIGS. 5A and 5B illustrate a reconstruction of a sweep recorded with the ultrasound device 21 being slowly pushed towards the bone and released several times. The sweeps in shown in FIGS. 5A and 5B are expanded along the object 76 to better visualize the motion with sweeps moving perpendicular to the bone only used for calibration. The f-CNN identifies and segments the bone surface in the manner previously described (step 102). A point cloud is extracted considering the tracking information of each frame. In other words, a point cloud is created (step 120) based on the tracked position of the ultrasonic probe 21 tracked relative to, for example, the localizer 34 of the surgical navigation system 20. A set of values is created or calculated by projecting the point cloud to a vector (step 122). In one example, the vector is a three-dimensional vector oriented parallel to the average direction of ultrasound scanlines.

FIG. 5A shows a reconstruction of an object 76 for an ultrasound sweep before optimization, and FIG. 5B shows a reconstruction of the object 76 after optimization. The temporal lag is computed (step 124) by choosing a value which minimizes variance of the set of values and provides the cost function at a global minimum at the optimization of the temporal lag, as shown in FIG. 5C (right). In one example, the standard deviation of repeated calibrations on recorded sweeps from human femur is two milliseconds. Temporal calibration is adapted to be performed automatically in real-time by, for example, the processor 52 of the navigation system 20.

With the workflow 100 as described above, superior spatial and temporal information quality in ultrasound is achieved for registration to the co-modality imaging. Subsequent to the real-time bone identification and segmentation, speed-of-sound calibration, and spatial and temporal calibration, the ultrasound imaging may be automatically registered to the co-modality imaging (step 108). In certain embodiments, the registration is formulated as a point-to-surface distance minimization problem. More specifically, the sum of the absolute distance of all points extracted from the calibrated intraoperative ultrasound image to the preoperative image segmented bone surface are minimized. This point-to-surface distance minimization problem may be solved via a global optimizer to avoid local minima and allow for automatic initialization during surgery. One suitable global optimizer may be DiRect as disclosed in Jones, D. R., et al., *Lipschitzian optimization without the lipschitz constant*, Journal of Optimization Theory and Applications 79(1) (1993) 157-181, the entire contents are herein incorporated by reference. In one example, a bounding search space was set to [−300 mm; 300 mm] for translations and [−100°; 100°] for rotations. In certain embodiments, a signed distance transform from the CT image segmentation may be precomputed for faster processing and evaluation. Once the global optimizer has found a suitable minimum, the transformation estimate is refined with a more local optimizer after removing the outliers—points which are further away than a predetermined distance after the first registration (e.g., five millimeters). One suitable local optimizer may be the Nelder-Mead method as described in Nelder, J. A., et al., *A simplex method for function minimization*, The computer journal 7(4) (1965) 308-313, the entire contents of which are herein incorporated by reference. Similar to the intraoperative ultrasound imaging, the preoperative image may require segmentation prior to registration. The CT image segmentation may be performed automatically or manually. Further, the CT image segmentation, particularly when performed manually, may be refined to provide a voxel-wise accurate bone surface, which may not be present when axial slices based on manual segmentations are stacked in three dimensions. In certain embodiments, the image segmentation may be refined using a three-dimensional guided filter to perform fast and precise image matting in three dimensions, and the bone surface may be extracted using a marching cubes algorithm.

Example I

A 4×4 wire grid was created on Perklab fCal 3 phantom and immersed in a water tank with 22.5° C. temperature. Based on the temperature and salinity of the water, expected sound speed was 1490 milliseconds (ms). Three ultrasound imaging with −5°, 0°, and +5° angles were recorded from the wire grid with imaging depth of 13 centimeters (cm). Wires were positioned with 1 cm spacing at depth of 9 cm to 12 cm. Speed of sound was set to 1540 ms on ultrasound machine. Then the speed of sound calibration was performed on the steered frames (bone surface masking step was ignored in this experiment). The result value was 1493.8 ms, which is 0.25% error.

Example II

A CT scan of the bilateral lower extremities of two cadavers were acquired after implanting six multi-modal spherical fiducials into each of the bones of interest, namely pelvis, femur, and tibia. For recording freehand ultrasound sweeps an optical tracking camera was used with a reference tracking target fixed to the bone and another target on the ultrasound device 21. One-hundred forty-two tracked ultrasound sweeps were recorded by two orthopedic surgeons. Ultrasound imaging were recorded with different frame geometries, image enhancement filters, brightness, and dynamic contrast to assure that ultrasound bone detection algorithm does not over-fit to a specific bone appearance. Scan geometries consisted of linear, trapezoid, and steered compound images with 3 consecutive frames (−15°/0°/+15° or −20°/0°/+20°). For the steered sweeps, the three original steered frames (subframes), in order to perform online speed of sound calibration. All ultrasound imaging were recorded with a linear 128-element probe at 7.5 MHz center frequency on a Cephasonics cQuest Cicada system.

In order to generate a ground truth registration between the CT images and the US sweeps, the fiducials were also scanned just before the ultrasound sweep acquisition, by accessing them with a dedicated hollow halfsphere fiducial tracking pointer. On the CT scans, the fiducial positions were extracted with an automatic algorithm based on a sub-voxel accurate sphere fitting. Point-correspondence registration then yielded a rigid transformation which is our Ground Truth. We obtained sub-mm accuracy in ground truth registration error (defined as the average residual distance between the CT and tracked fiducial positions after registration) with an average of 0.69 mm, and a median of 0.28 mm.

TABLE 1

Unsigned median registration errors of all sweeps (respectively surface registration error, fiducial errors, and relative error for the three translations and rotations parameters). All errors are given in mm except rotations errors which are given in degrees.

| Case | Error Surface | Error Fid. | Error T1* | Error T2* | Error T3* | Error R1 | Error R2 | Error R3 |
|------|---------------|------------|-----------|-----------|-----------|----------|----------|----------|
| Tibia | 0.41 | 2.00 | 3.83 | 1.15 | 2.38 | 0.38 | 0.21 | 1.69 |
| Femur | 0.52 | 2.12 | 1.50 | 1.79 | 0.82 | 0.27 | 0.47 | 0.72 |
| Pelvis | 0.56 | 2.63 | 1.70 | 4.33 | 3.39 | 1.33 | 0.67 | 0.92 |
| Mean | 0.49 | 2.25 | | | | | | |

*Errors depend on reference coordinate system (bone mesh center was used).

With segmented and calibrated ultrasound image registered with the pre-operative image, the surgical navigation system 20 may proceed with the surgical procedure. In one embodiment, the navigation system is part of a robotic surgical system for treating tissue (see FIG. 1). In one example, a cutting system of the robotic surgical system is used to prepare bone for surgical implants such as hip and knee implants, including unicompartmental, bicompartmental, or total knee implants. Some of these types of implants are shown in U.S. Pat. No. 9,381,085 entitled, "Prosthetic Implant and Method of Implantation", the disclosure of which is hereby incorporated by reference in its entirety.

It is to be appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. An ultrasound imaging system comprising:
an ultrasound imaging device comprising a transducer configured to generate ultrasound imaging of a bone region by propagation of ultrasound waves to the bone region; and
one or more controllers coupled to the ultrasound imaging device and being configured to:
generate, with the ultrasound imaging device, a first steered frame and a second steered frame, wherein the first steered frame and the second steered frame are directed towards the bone region at different angles from one another and are superimposed with one another, and wherein each of the first steered frame and the second steered frame include pixel intensities of the bone region;
apply the pixel intensities of each of the first steered frame and the second steered frame to a cost function that is configured to: minimize differences in the pixel intensities between the first steered frame and the second steered frame, using propagation speed as an input parameter; and output an estimated propagation speed of ultrasound waves to the bone region that optimizes an appearance of the first steered frame and the second steered frame; and
calibrate the ultrasound imaging device based on the estimated propagation speed.

2. The ultrasound imaging system of claim 1, wherein the one or more controllers are further configured to:
generate, with the ultrasound imaging device, a third frame that is angled between the first and second steered frames, wherein the third frame includes pixel intensities of the bone region; and
further apply the pixel intensities of the third frame to the cost function.

3. The ultrasound imaging system of claim 2, wherein:
the cost function is further configured to minimize differences in pixel intensities between (1) the first steered frame and the third frame and (2) the second steered frame and the third frame, using propagation speed as the input parameter.

4. The ultrasound imaging system of claim 2, wherein the one or more controllers further implement the cost function by being configured to:
compute a first difference between the pixel intensities of the first steered frame and the third frame;
compute a second difference between the pixel intensities of the second steered frame and the third frame;
compute a sum of the first difference and second difference;
optimize the sum to minimize the cost function; and
output the estimated propagation speed based on the optimized sum.

5. The ultrasound imaging system of claim 2, wherein the third frame is angled perpendicular to the bone region.

6. The ultrasound imaging system of claim 1, wherein the one or more controllers are further configured to mask a non-bone region prior to application of the pixel intensities of the first steered frame and the second steered frame to the cost function.

7. A method of operating an ultrasound imaging system, the ultrasound imaging system comprising an ultrasound imaging device including a transducer configured to generate ultrasound imaging of a bone region by propagation of ultrasound waves to the bone region, and one or more controllers coupled to the ultrasound imaging device, the method comprising the one or more controllers:
generating, with the ultrasound imaging device, a first steered frame and a second steered frame, wherein the first steered frame and the second steered frame are directed towards the bone region at different angles from one another and are superimposed with one another, and wherein each of the first steered frame and the second steered frame include pixel intensities of the bone region;

applying the pixel intensities of each of the first steered frame and the second steered frame to a cost function that: minimizes differences in the pixel intensities between the first steered frame and the second steered frame, using propagation speed as an input parameter; and outputs an estimated propagation speed of ultrasound waves to the bone region for optimizing an appearance of the first steered frame and the second steered frame; and calibrating the ultrasound imaging device based on the estimated propagation speed.

8. The method of claim 7, comprising the one or more controllers:

generating, with the ultrasound imaging device, a third frame that is angled between the first and second steered frames, wherein the third frame includes pixel intensities of the bone region; and further applying the pixel intensities of the third frame to the cost function.

9. The method of claim 8, further comprising the one or more controllers implementing the cost function for outputting the estimated propagation speed by minimizing differences in the pixel intensities between (1) the first steered frame and the third frame and (2) the second steered frame and the third frame, using propagation speed as the input parameter.

10. The method of claim 8, comprising the one or more controllers implementing the cost function by:

computing a first difference between the pixel intensities of the first steered frame and the third frame;

computing a second difference between the pixel intensities of the second steered frame and the third frame;

computing a sum of the first difference and second difference;

optimizing the sum to minimize the cost function; and outputting the estimated propagation speed based on the optimized sum.

11. The method of claim 7, comprising the one or more controllers masking a non-bone region prior to applying the pixel intensities of each of the first steered frame and the second steered frame to the cost function.

12. A computer-implemented method for calibrating ultrasound imaging directed towards a bone region, the method comprising:

generating, with the ultrasound imaging, a first steered frame and a second steered frame, wherein the first steered frame and the second steered frame are directed towards the bone region at different angles from one another and are superimposed with one another, and wherein each of the first steered frame and the second steered frame include pixel intensities of the bone region;

applying the pixel intensities of each of the first steered frame and the second steered frame to a cost function that: minimizes differences in the pixel intensities between the first steered frame and the second steered frame, using propagation speed as an input parameter; and outputs an estimated propagation speed of ultrasound waves to the bone region for optimizing an appearance of the first steered frame and the second steered frame; and calibrating the ultrasound imaging based on the estimated propagation speed.

13. The method of claim 12, further comprising:

identifying, from the ultrasound imaging, a third frame that is angled between the first and second steered frames, wherein the third frame includes pixel intensities of the bone region; and further applying the pixel intensities of the third frame to the cost function.

14. The method of claim 13, comprising the cost function outputting the estimated propagation speed by further minimizing differences in the pixel intensities between (1) the first steered frame and the third frame and (2) the second steered frame and the third frame, using propagation speed as the input parameter.

* * * * *